US009999405B2

(12) United States Patent
Pintoffl et al.

(10) Patent No.: US 9,999,405 B2
(45) Date of Patent: Jun. 19, 2018

(54) METHOD AND SYSTEM FOR ENHANCED VISUALIZATION OF A CURVED STRUCTURE BY AUTOMATICALLY DISPLAYING A RENDERED VIEW OF A CURVED IMAGE SLICE

(71) Applicant: General Electric Company, Schenectady, NY (US)

(72) Inventors: Klaus Pintoffl, Oberosterreich (AT); Christian Fritz Perrey, Oberosterreich (AT); Jos Stas, Flemish Brabant (BE)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days. days.

(21) Appl. No.: 15/044,264

(22) Filed: Feb. 16, 2016

(65) Prior Publication Data
US 2017/0236248 A1 Aug. 17, 2017

(51) Int. Cl.
*G06T 3/00* (2006.01)
*A61B 8/08* (2006.01)
(Continued)

(52) U.S. Cl.
CPC ............ *A61B 8/523* (2013.01); *A61B 5/4325* (2013.01); *A61B 8/08* (2013.01); *A61B 8/466* (2013.01);
(Continued)

(58) Field of Classification Search
None
See application file for complete search history.

(56) References Cited

U.S. PATENT DOCUMENTS 5,590,654 A 1/1997 Prince
6,468,218 B1 10/2002 Chen et al.
(Continued)

FOREIGN PATENT DOCUMENTS

WO WO 2016016227 A1 * 2/2016 ............... G06T 7/12
WO WO 2016067260 A1 * 5/2016 ............ A61B 8/0841

OTHER PUBLICATIONS

Langer et al, "Imaging of the Female Pelvis through the Life Cycle", RSNA RadioGraphics, 32(6), Oct. 2012.*
(Continued)

*Primary Examiner* — Ulka Chauhan
*Assistant Examiner* — Patrick F Valdez
(74) *Attorney, Agent, or Firm* — McAndrews, Held & Malloy, Ltd.; Jacob Groethe; David Bates

(57) ABSTRACT

A processor identifies a curved structure in three-dimensional medical image data. The processor selects a plane in the three-dimensional medical image data based at least in part on the identified curved structure. The processor defines a curved image slice in the selected plane based at least in part on the identified curved structure. The curved image slice may be defined by drawing a pair of curved lines on opposite sides of the identified curved structure in the selected plane. The distance between the pair of curved lines may define a thickness of the curved image slice. The processor generates a rendered image of the defined curved image slice. The rendered image may be generally perpendicular to the selected plane. The rendered image and/or the selected plane having the pair of curved lines superimposed on opposite sides of the identified curved structure may be presented at a display system.

20 Claims, 4 Drawing Sheets

(51) Int. Cl.
*A61B 8/00* (2006.01)
*A61B 5/00* (2006.01)
*G06T 19/00* (2011.01)

(52) U.S. Cl.
CPC ............ *A61B 8/483* (2013.01); *A61B 8/5207* (2013.01); *G06T 19/00* (2013.01); *A61B 2576/02* (2013.01); *G06T 2210/41* (2013.01); *G06T 2219/008* (2013.01)

(56) References Cited

U.S. PATENT DOCUMENTS

| | | |
|---|---|---|
| 6,819,782 B1 | 11/2004 | Imagawa et al. |
| 2007/0161905 A1 | 7/2007 | Munrow |
| 2008/0055305 A1* | 3/2008 | Blank ..................... G06T 15/08 345/419 |
| 2009/0079738 A1* | 3/2009 | Liao ........................ G06T 19/00 345/427 |
| 2009/0097723 A1 | 4/2009 | Washburn et al. |
| 2010/0214283 A1* | 8/2010 | Lobregt .................. G06T 15/08 345/419 |
| 2012/0288172 A1* | 11/2012 | Perrey .................... A61B 8/145 382/131 |
| 2013/0022255 A1* | 1/2013 | Chen ........................ G06K 9/34 382/131 |
| 2013/0150718 A1* | 6/2013 | Dixon .................. A61B 8/4483 600/443 |
| 2017/0007207 A1* | 1/2017 | Gauthier ............. G01S 7/52084 |

OTHER PUBLICATIONS

Saroul et al, "Distance Preserving Flattening of Surface Sections", IEEE Trans. on Visualization and Computer Graphics, 12(1), pp. 26-35, 2006.*

* cited by examiner

METHOD AND SYSTEM FOR ENHANCED VISUALIZATION OF A CURVED STRUCTURE BY AUTOMATICALLY DISPLAYING A RENDERED VIEW OF A CURVED IMAGE SLICE

FIELD

Certain embodiments of the invention relate to ultrasound imaging. More specifically, certain embodiments of the invention relate to a method and system for enhanced visualization of a curved structure, such as a uterine cavity. The method and system may be operable to detect a curved line, such as the endometrium of a uterus, in three-dimensional ultrasound image data, define a curved image slice corresponding with the detected curved line, and automatically generate and display a rendered view of the curved image slice.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Uterine abnormalities are associated with an increased risk of miscarriage, infertility, premature birth, and caesarean delivery, among other things. Ultrasound imaging may be helpful as part of a routine gynecology examination and before starting in vitro fertilization to evaluate the uterus for possible anatomical abnormalities. For example, ultrasound imaging may be used to identify congenital malformations, such as septate, bicornuate, unicornuate, uterus didelphys, and the like. As another example, ultrasound imaging can be used to identify tumors, such as myomas, among other things.

Conventional transvaginal 2D sonography has been shown to be a good screening tool for uterine abnormalities. However, the ability to distinguish between different types of abnormalities using 2D sonography is limited and operator dependent. For example, it is typically not possible to obtain the coronal view of the uterus because of the position of the uterus and limitations associated with positioning a 2D ultrasound probe transvaginally. Moreover, the uterine cavity cannot be fully documented in a single ultrasound image of a 2D scan. An ultrasound operator may use 3D ultrasound to reconstruct parts of the uterine cavity within the coronal plane. However, selecting a sectional plane in 3D image data may not illustrate the full uterine cavity because the uterine cavity is typically curved.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY

A system and/or method is provided for enhanced visualization of a curved structure by automatically displaying a rendered view of a curved image slice, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION

Figure 1:
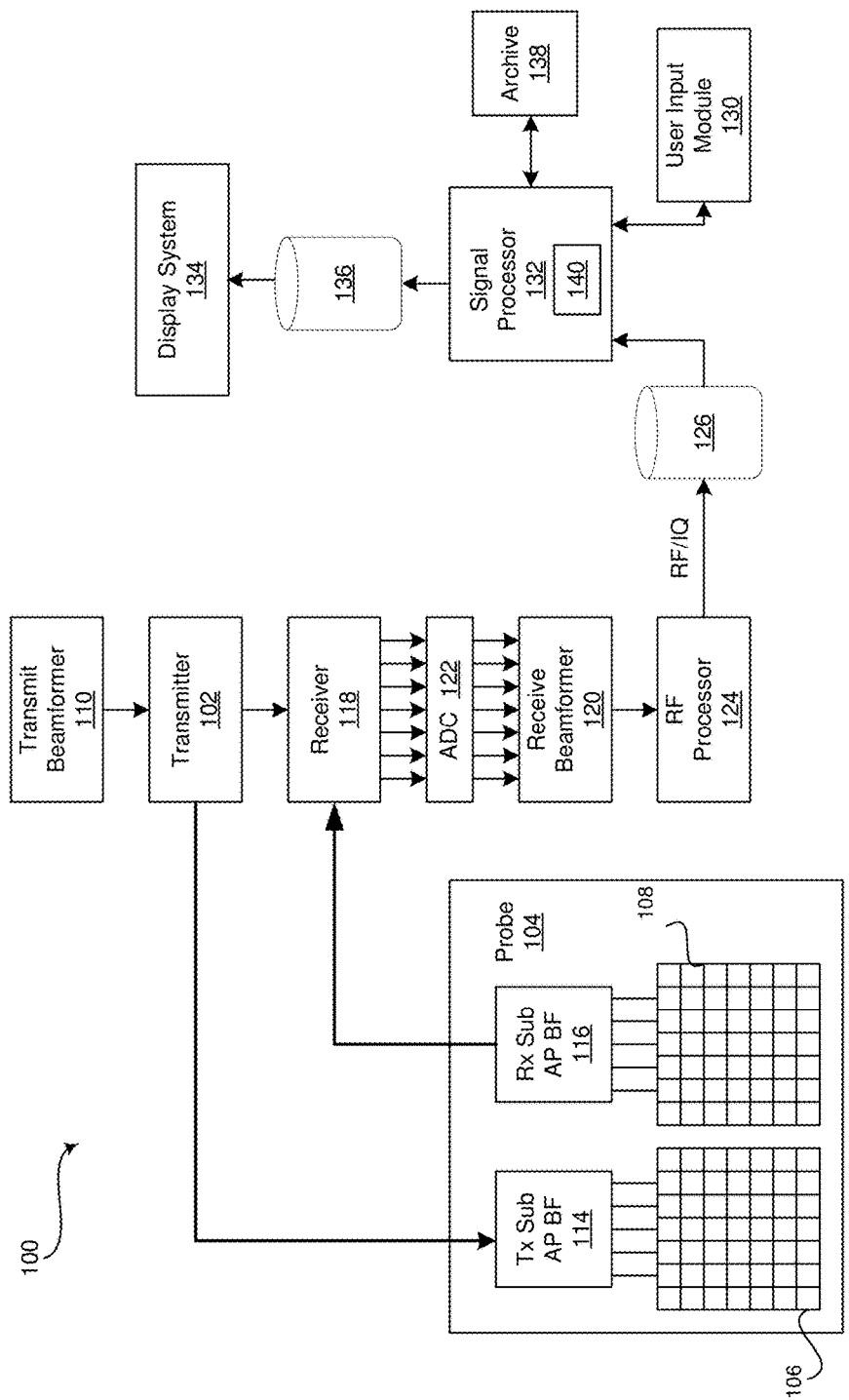
FIG. 1 is a block diagram of an exemplary ultrasound system that is operable to provide enhanced visualization of a curved structure by automatically displaying a rendered view of a curved image slice, in accordance with various embodiments.

Certain embodiments may be found in a method and system for providing enhanced visualization of a curved structure, such as a uterine cavity, by automatically displaying a rendered view of a curved image slice. For example, various aspects have the technical effect of automatically detecting a curved line, such as the endometrium of a uterus, in a selected plane (e.g., the insonation plane such as the mid-sagittal plane) of 3D ultrasound image data. Moreover, certain embodiments have the technical effect of defining a curved image slice corresponding with the detected curved line. Furthermore, various embodiments have the technical effect of enhancing visualization of a curved structure, such as a uterine cavity, by automatically generating and displaying a rendered view of the curved image slice in a plane generally perpendicular to the selected plane.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Moreover, although certain embodiments in the foregoing description may describe the imaging modality and/or images in the context of ultrasound, for example, unless so claimed, the scope of various aspects of the present invention should not be limited to ultrasound imaging modalities and images and may additionally and/or alternatively be applicable to any suitable medical imaging modality and image, such as computed tomography, magnetic resonance, x-ray, and the like.

Additionally, although certain embodiments in the foregoing description may describe enhancing visualization of a uterine cavity, for example, unless so claimed, the scope of various aspects of the present invention should not be limited to a uterine cavity and may additionally and/or alternatively be applicable to any suitable curved structure, such as a spine, among other things.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to provide enhanced visualization of a curved structure by automatically displaying a rendered view 320 of a curved image slice 318, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, and a display system 134.

The transmitter 102 may comprise suitable logic, circuitry, interfaces and/or code that may be operable to drive an ultrasound probe 104. The ultrasound probe 104 may comprise a three dimensional (3D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, surgical instrument data, scan parameters, settings, configuration parameters, render settings, change scan mode, select an image display mode, interact with curved lines superimposed over image data to define an image slice for rendering, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134.

The signal processor 132 may comprise suitable logic, circuitry, interfaces and/or code that may be operable to process ultrasound scan data (i.e., RF signal data or IQ data pairs) for generating ultrasound images for presentation on a display system 134. The signal processor 132 is operable to perform one or more processing operations according to a plurality of selectable ultrasound modalities on the acquired ultrasound scan data. In an exemplary embodiment of the invention, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. The processed image data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise an image rendering module 140.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an image rendering module 140 that comprises suitable logic, circuitry, interfaces and/or code that may be operable to automatically generate a rendered view of a curved structure, such as a uterine cavity, from 3D ultrasound data. The image rendering module 140 may be activated, for example, in response to the signal processor 132 receiving a selection of a render image display mode via the user input module 130. The image rendering module 140 may receive 3D ultrasound data in real-time or near real-time as acquired by the ultrasound probe 104 and/or may retrieve 3D ultrasound data from an archive 138, such as a local archive, a Picture Archiving and Communication System (PACS), or any suitable device for storing images and related information.

Figure 3:
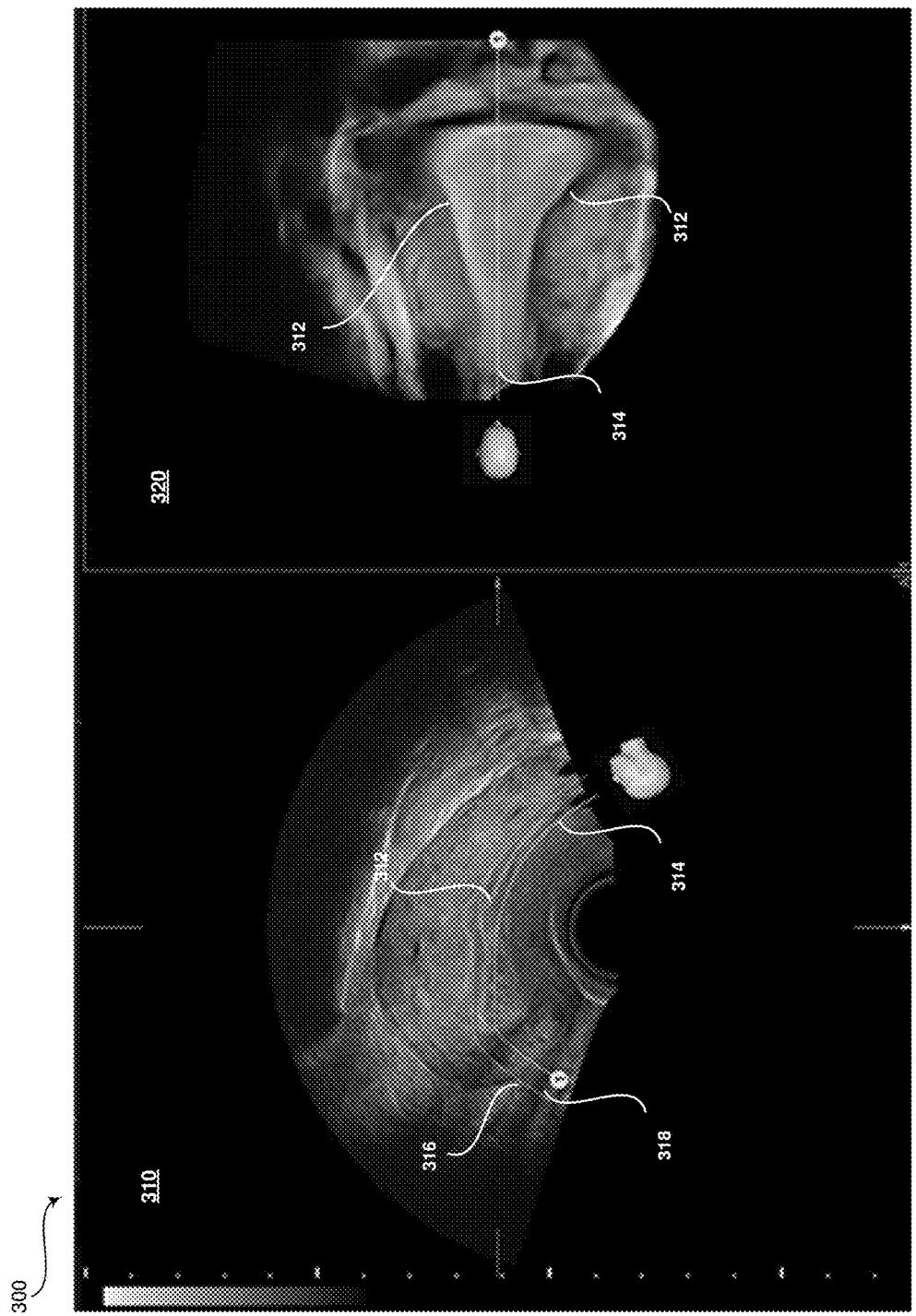
FIG. 3 is a screenshot of an exemplary dual-view image display including a selected plane and a rendered image, in accordance with exemplary embodiments.

The image rendering module 140 may comprise suitable logic, circuitry, interfaces and/or code that may be operable to process the 3D ultrasound scan data to identify a curved line or structure, such as the endometrium 312 of a uterus as shown in FIG. 3. For example, the image rendering module 140 may apply image detection techniques and/or algorithms to automatically identify the endometrium 312 in the 3D ultrasound image data. The image detection techniques and/or algorithms may search the image data for the curved line 312 corresponding with the endometrium. The image rendering module 140 may select a plane 310 in the three-dimensional image data based on the identified curved structure or line 312. For example, the rendering module 140 may select the plane 310 providing an optimal view, such as a centered view, of the curved endometrium line 312. The selected plane 310 may be, for example, at or near the insonation plane, which is typically the mid-sagittal plane. Additionally and/or alternatively, the rendering module 140 may begin at the insonation plane and rotate about the Y-axis to select the plane 310 with the optimal view of the curved line 312.

The image rendering module 140 may comprise suitable logic, circuitry, interfaces and/or code that may be operable to define a curved image slice 318 in the 3D ultrasound image data corresponding with the identified curved endometrium line 312. The image rendering module 140, for example, may draw a pair of curved lines 314, 316 on opposite sides of the identified curved endometrium line 312 in the selected plane 310 as illustrated in FIG. 3. The distance between the pair of curved lines 314, 316 may be based on a default or user-defined slice thickness, such as 5 millimeters or any suitable slice thickness. In various embodiments, the pair of curved lines 314, 316 may be superimposed or overlaid on the selected image plane 310 and provided to the image buffer 136 and/or the display system 134. The image data between the pair of curved lines 314, 316 may define the curved image slice 318 in the 3D ultrasound image data.

The image rendering module 140 may comprise suitable logic, circuitry, interfaces and/or code that may be operable to automatically generate a rendered image 320 of the defined curved image slice 318 in a plane generally perpendicular to the selected plane 310. The generation of the rendered image 320 may be based, at least in part, on render settings. For example, the render settings may include surface rendering, maximum intensity projection, minimum intensity projection, X-ray mode, light mode, or any suitable render setting and/or combinations of render settings. In various embodiments, the rendered image 320 of the curved image slice 318 may correspond generally with the coronal plane. The image rendering module 140 may provide the rendered image 320 to the image buffer 136 and/or the display system 134. For example, the selected image plane 310 with the overlaid pair of curved lines 314, 316 and the rendered image 320 may be presented at the display system 134 in a dual-view image display mode as illustrated in FIG. 3. Additionally and/or alternatively, the selected image plane 310 and rendered image 320 may be presented at different display monitors or separately at different times, among other things.

The image rendering module 140 may comprise suitable logic, circuitry, interfaces and/or code that may be operable to manipulate the display of the medical images 310, 320 based on user interaction with the curved lines 314, 316 and/or the render settings. For example, an ultrasound operator may use the user input module 130 to move the superimposed curved lines 314, 316, adjust the slice thickness, and/or select different render modes or combinations of render modes. The image rendering module 140 dynamically updates the medical images 310, 320 presented at the display system 134 based on the instructions received from the user input module 130. The image rendering module 140 may store the processed selected plane 310 and/or rendered image 320 at the archive 138.

FIG. 3 is a screenshot of an exemplary dual-view image display 300 including a selected plane 310 and a rendered image 320, in accordance with exemplary embodiments. Referring to FIG. 3, the dual-view image display 300 comprises two medical images, which may be the selected plane 310 and a rendered volume 320 as described with reference to FIG. 1. For example, the selected plane 310 may be the plane selected by the rendering module 140 providing an optimal view of the curved endometrium line 312 and the rendered volume 320 may be the image generated by the rendering module 140 based on the defined curved image slice 318 in the plane generally perpendicular to the selected plane 310. The selected plane 310 may be at or near the insonation plane, which may be the mid-sagittal plane, for example. The dual-view image display 300 may be presented at the display system 134 by the image rendering module 140.

Still referring to FIG. 3, the dual-view image display 300 may present medical images 310, 320 of a uterus having an endometrium 312. For example, the selected plane 310 may show a mid-sagittal view of the uterus. The image rendering module 140 may define a curved image slice 318 in the selected plane 310 by identifying the curved endometrium line 312 and drawing a pair of curved lines 314, 316 on opposite sides of the endometrium line 312. For example, the curved image slice 318 may correspond with the image data between the pair of curved lines 314, 316. The width of the pair of curved lines 314, 316 may be based on a slice thickness. The slice thickness may be a default thickness, a pre-defined user-selected thickness, and/or a user-adjusted thickness to manipulate the images 310, 320 after the images 310, 320 are displayed. The image rendering module 140 may automatically generate the rendered image 320 of the defined curved image slice 318 in a plane generally perpendicular to the selected plane 310 based, at least in part, on render settings. For example, the rendered image 320 may provide a view of the full uterine cavity.

Figure 2:
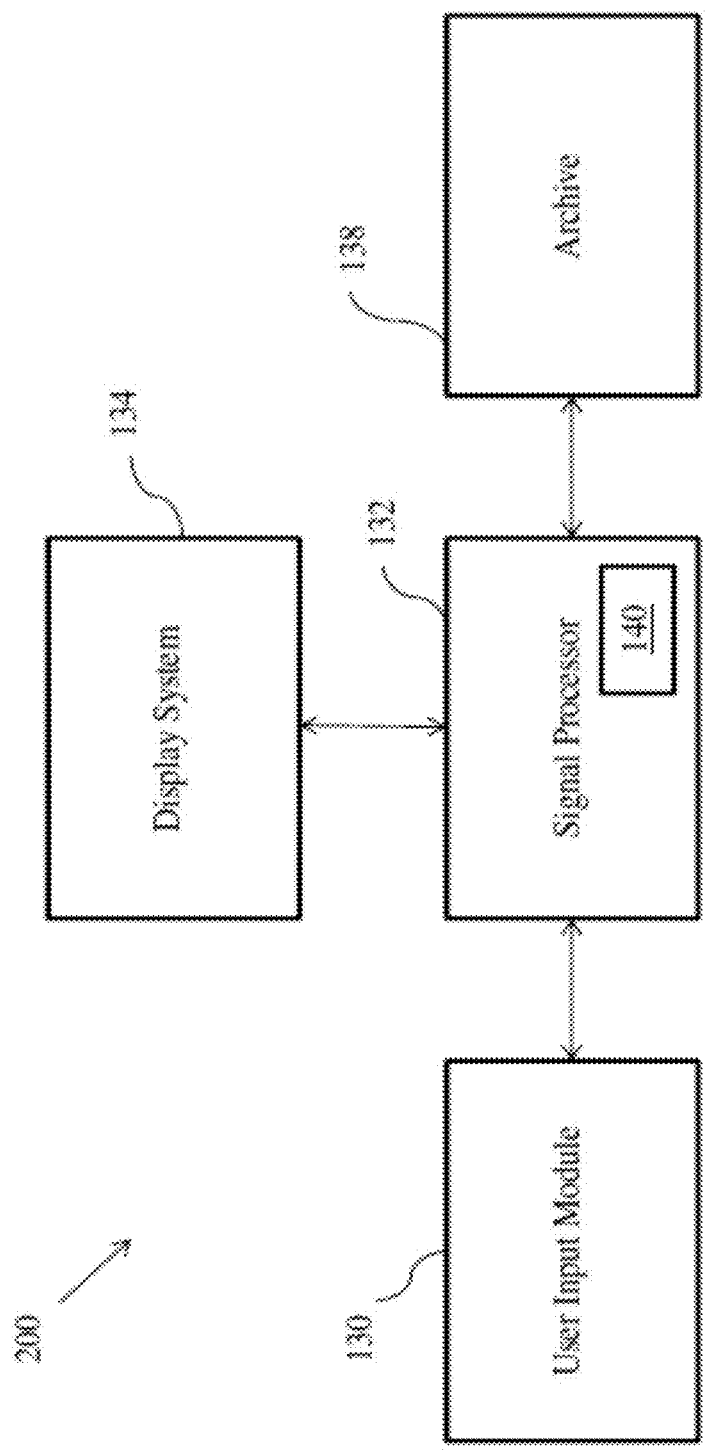
FIG. 2 is a block diagram of an exemplary medical workstation that is operable to provide enhanced visualization of a curved structure by automatically displaying a rendered view of a curved image slice, in accordance with certain embodiments.

FIG. 2 is a block diagram of an exemplary medical workstation 200 that is operable to provide enhanced visualization of a curved structure by automatically displaying a rendered view 320 of a curved image slice 318, in accordance with certain embodiments. In various embodiments, components of the medical workstation 200 may share various characteristics with components of the ultrasound system 100, as illustrated in FIG. 1 and described above. Referring to FIG. 2, the medical workstation 200 comprises a display system 134, a signal processor 132, an archive 138, and a user input module 130, among other things. Components of the medical workstation 200 may be implemented in software, hardware, firmware, and/or the like. The various components of the medical workstation 200 may be communicatively linked. Components of the medical workstation 200 may be implemented separately and/or integrated in various forms. For example, the display system 134 and the user input module 130 may be integrated as a touchscreen display.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as medical images, or any suitable information.

The signal processor 132 may be one or more central processing units, microprocessors, microcontrollers, and/or the like. The signal processor 132 may be an integrated component, or may be distributed across various locations, for example. The signal processor 132 comprises an image rendering module 140, as described above with reference to FIG. 1. The image rendering module 140 may be capable of receiving 3D ultrasound image data from an archive 138, automatically detecting a curved line 312 (e.g., an endometrium of a uterus) in 3D image data, selecting an optimal image plane 310, defining a curved image slice 318 corresponding with the detected curved line 312 in the selected image plane 310, automatically generating and displaying a rendered view 320 of the curved image slice 318 in a plane generally perpendicular to the selected plane 310 at a display system 134, and manipulating the rendered image 320 in response to input information from a user input module 130, among other things. The signal processor 132 and/or image rendering module 140 may be capable of executing any of the method(s) and/or set(s) of instructions discussed herein in accordance with the various embodiments, for example.

The archive 138 may be one or more computer-readable memories integrated with the medical workstation 200 and/or communicatively coupled (e.g., over a network) to the medical workstation 200, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores medical image data and instructions for detecting the endometrium 312, selecting the optimal image plane 310, defining the curved image slice 318, generating the rendered view 320, and manipulating the rendered view 320 in response to user input, for example.

The user input module 130 may include any device(s) capable of communicating information from a user and/or at the direction of the user to the signal processor 132 of the medical workstation 200, for example. The user input module 130 may include a mousing device, keyboard, touch panel, camera, buttons, switches, voice recognition, and/or any other device capable of receiving a user directive.

Figure 4:
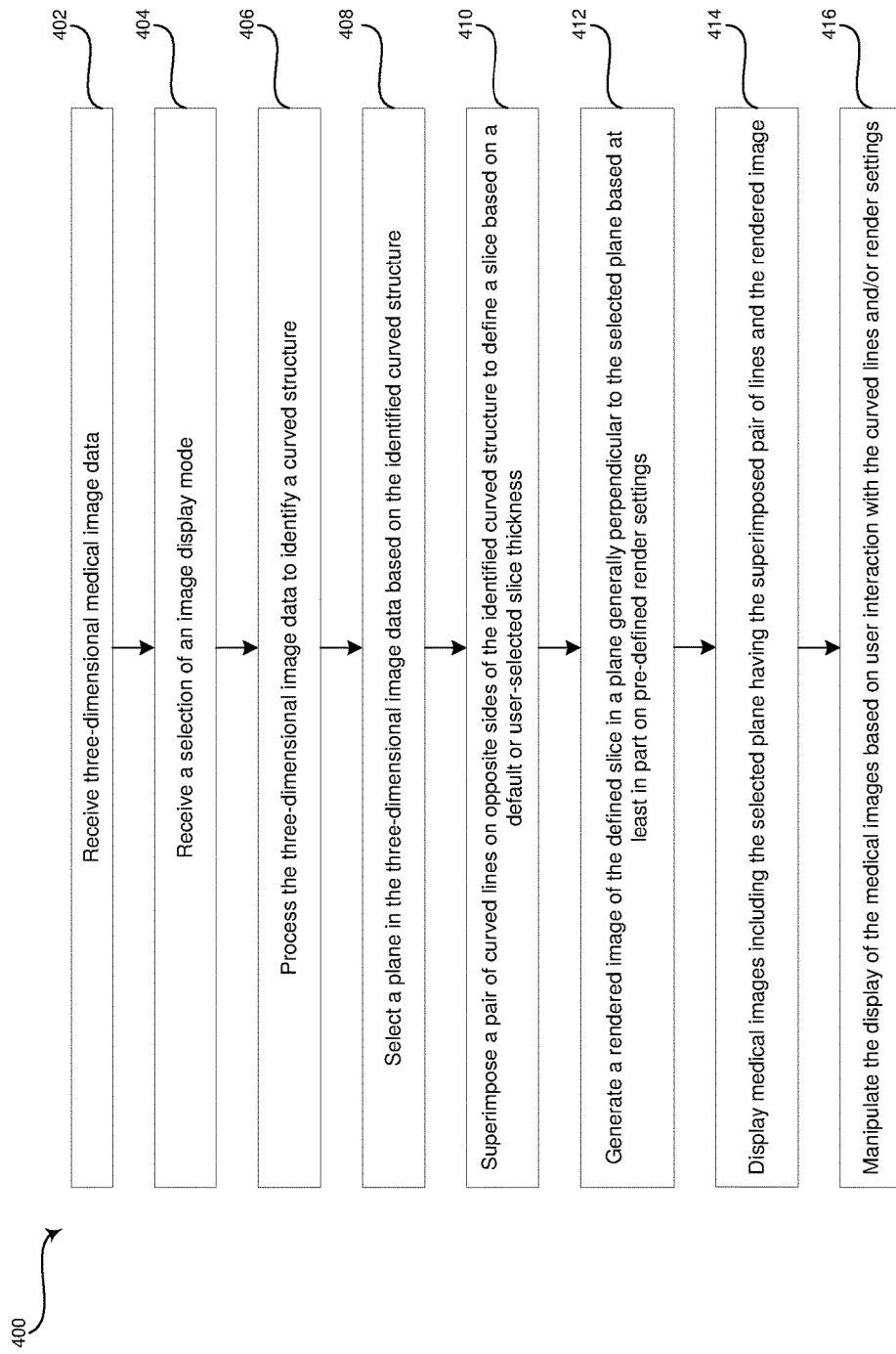
FIG. 4 is a flow chart illustrating exemplary steps that may be utilized for providing enhanced visualization of a curved structure by automatically displaying a rendered view of a curved image slice, in accordance with various embodiments.

FIG. 4 is a flow chart 400 illustrating exemplary steps 402-416 that may be utilized for providing enhanced visualization of a curved structure by automatically displaying a rendered view 320 of a curved image slice 318, in accordance with various embodiments. Referring to FIG. 4, there is shown a flow chart 400 comprising exemplary steps 402 through 416. Certain embodiments of the present invention may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

In step 402, the signal processor 132 may receive 3D medical image data. For example, an ultrasound system 100 may acquire 3D ultrasound data that is provided to the signal processor 132 as described above with regard to FIG. 1. As another example, the signal processor 132 of the ultrasound system 100 or a medical workstation 200 may retrieve the 3D medical image data from an archive 138. The medical image data may be computed tomography, magnetic resonance, x-ray, or any suitable 3D medical image data. The medical image data may be of a curved structure, such as a uterine cavity, spine, or any suitable curved structure.

In step 404, the signal processor 132 may receive a selection of an image display mode. For example, the signal processor 132 may receive a selection of a render image display mode via a user input module 130. The selection of the render image display mode may activate the image rendering module 140 to automatically display a rendered view of a curved structure, such as a uterine cavity, from the received 3D medical image data by performing one or more of steps 406 through 416 below. The selection via the user input module 130 may be a depression of a button at a control panel of an ultrasound system 100, a mouse-click of a button displayed at a display system 134 of a medical workstation, or any suitable user selection.

In step 406, the image rendering module 140 of the signal processor 132 may process the 3D medical image data to identify a curved structure 312. For example, the image rendering module 140 may apply image detection techniques and/or algorithms to automatically identify an endometrium 312 of a uterine cavity in the received 3D image data. The image detection techniques and/or algorithms may search the image data for structure, such as a curved line, corresponding with the endometrium 312 or other curved structure.

In step 408, the image rendering module 140 of the signal processor 132 may select a plane 310 in the 3D medical image data based on the identified curved structure 312. For example, the image rendering module 140 may select a plane at or near the insonation plane, usually the mid-sagittal plane, providing a centered view of the curved line 312, such as the endometrium of a uterus. Additionally and/or alternatively, the image rendering module 140 may begin with the insonation plane and rotate the image data about the Y-axis to select the plane 310.

In step 410, the image rendering module 140 of the signal processor 132 may superimpose or overlay a pair of curved lines 314, 316 on opposite sides of the identified curved structure 312 to define a slice 318 based on a default or user-selected slice thickness. For example, the image rendering module 140 may draw the first line 314 on a first side of the curved structure 312, such as the endometrium of the uterus, and the second line 316 on a second side of the curved structure 312. The image data between the curved lines 314, 316 defines an image slice 318 for rendering. The distance between each curved line 314, 316 and the curved structure 312 may be the same. The distance between the curved lines 314, 316 is the slice thickness. The slice thickness may be a user-selected value or a default value, such as 5 millimeters or any suitable thickness.

In step 412, the image rendering module 140 of the signal processor 132 may generate a rendered image 320 of the defined slice 318 in a plane generally perpendicular to the selected plane 310 based at least in part on pre-defined render settings. For example, the image rendering module 140 may generate the rendered image 320 in generally the coronal plane. The rendered image 320 may illustrate a cross-section of the full uterine cavity. The rendered image 320 may be based on render settings, such as surface rendering, maximum intensity projection, minimum intensity projection, X-ray mode, light mode, or any suitable render setting and/or combinations of render settings.

In step 414, the image rendering module 140 of the signal processor 132 may display medical images including the selected plane 310 having the superimposed pair of lines 314, 316 and the rendered image 320. For example, the image rendering module 140 may present the medical images 310, 320 in a dual-view display 300 at a display system 134. Additionally and/or alternatively, the medical images 310, 320 may be displayed separately and/or at different display monitors of the display system 134.

In step 416, the image rendering module 140 of the signal processor 132 may manipulate the display of the medical images 310, 320 based on user interaction with the curved lines 314, 316 and/or render settings. For example, an ultrasound or medical workstation operator may provide the image rendering module 140 instructions for modifying the medical images 310, 320 via a user input module 130. The operator can, for example, move the curved lines 314, 316, change the slice thickness, and/or select different render settings, among other things. The image rendering module 140 may apply the changes to dynamically update the medical images 310, 320 presented at the display system 134.

Aspects of the present invention provide a method 400 and system 100, 200 for providing enhanced visualization of a curved structure. In accordance with various embodiments, the method 400 comprises identifying 406, by a processor 132, 140, a curved structure 312 in three-dimensional medical image data. The method 400 comprises selecting 408, by the processor 132, 140, a plane 310 in the three-dimensional medical image data based at least in part on the identified curved structure 312. The method 400 comprises defining 410, by the processor 132, 140, a curved image slice 318 in the selected plane 310 based at least in part on the identified curved structure 312. The method 400 comprises generating 410, by the processor 132, 140, a rendered image 320 of the defined curved image slice 318.

In a representative embodiment, the method 400 comprises acquiring 402, by an ultrasound device 100, the three-dimensional medical image data. In certain embodiments, the method 400 comprises receiving 404, by the processor 132, 140, a selection of a render image display mode to initiate the identification 406 of the curved structure 312 in the three-dimensional medical image data. In various embodiments, the curved image slice 318 is defined by drawing a pair of curved lines 314, 316 on opposite sides of the identified curved structure 312 in the selected plane 310. The distance between the pair of curved lines 314, 316 may define a thickness of the curved image slice 318.

In certain embodiments, the method 400 comprises presenting 414, at a display system 134, one or more of the rendered image 320 of the defined curved image slice 318 and the selected plane 310 having a pair of curved lines 314, 316 superimposed on opposite sides of the identified curved structure 312. The pair of curved lines 314, 316 corresponds with the curved image slice 318. In a representative embodiment, the rendered image 320 and the selected plane 310 are presented at the display system 134. The processor 132, 140 dynamically updates one or more of the rendered image 320 and the selected plane 310 in response to a user input at least one of changing a position of the pair of curved lines 314, 316 and changing render settings. In various embodiments, the curved structure 312 is an endometrium of a uterus. In certain embodiments, the selected plane 310 is a mid-sagittal plane. In a representative embodiment, the rendered image 320 is generally perpendicular to the selected plane 310.

Various embodiments provide a system 100, 200 for providing enhanced visualization of a curved structure. The system 100, 200 comprises a processor 132, 140 configured to identify a curved structure 312 in three-dimensional medical image data. The processor 132, 140 is configured to select a plane 310 in the three-dimensional medical image data based at least in part on the identified curved structure 312. The processor 132, 140 is configured to define a curved image slice 318 in the selected plane 310 based at least in part on the identified curved structure 312. The processor 132, 140 is configured to generate a rendered image 320 of the defined curved image slice 318.

In a representative embodiment, the system 100, 200 comprises a display system 134 configured to present one or more of the rendered image 320 of the defined curved image slice 318 and the selected plane 310 having a pair of curved lines 314, 316 superimposed on opposite sides of the identified curved structure 312. The pair of curved lines 314, 316 corresponds with the curved image slice 318. In certain embodiments, the rendered image 320 and the selected plane 310 are presented at the display system 134. The processor 132, 140 is configured to dynamically update one or more of the rendered image 320 and the selected plane 310 in response to a user input at least one of changing a position of the pair of curved lines 314, 316 and changing render settings. In various embodiments, the system 100, 200 comprises an ultrasound device 100 configured to acquire the three-dimensional medical image data.

In certain embodiments, the processor 132, 140 is configured to define the curved image slice 318 by drawing a pair of curved lines 314, 316 on opposite sides of the identified curved structure 312 in the selected plane 310. The distance between the pair of curved lines 314, 316 defines a thickness of the curved image slice 318. In a representative embodiment, the curved structure 312 is an endometrium of a uterus. In various embodiments, the selected plane 310 is a mid-sagittal plane and/or the rendered image 320 is generally perpendicular to the selected plane 310.

Certain embodiments provide a non-transitory computer readable medium having stored thereon, a computer program having at least one code section. The at least one code section is executable by a machine for causing the machine to perform steps. The steps 400 include identifying 406 a curved structure 312 in three-dimensional medical image data. The steps 400 include selecting 408 a plane 310 in the three-dimensional medical image data based at least in part on the identified curved structure 312. The steps 400 include defining 410 a curved image slice 318 in the selected plane 310 based at least in part on the identified curved structure 312. The steps 400 include generating 410 a rendered image 320 of the defined curved image slice 318.

In a representative embodiment, the steps 400 include displaying 414 one or more of the rendered image 320 of the defined curved image slice 318 and the selected plane 310 having a pair of curved lines 314, 316 superimposed on opposite sides of the identified curved structure 312. The pair of curved lines 314, 316 corresponds with the curved image slice 318. In various embodiments, the curved structure 312 is an endometrium of a uterus, the selected plane 310 is a mid-sagittal plane, and/or the rendered image 320 is generally perpendicular to the selected plane 310. In certain embodiments, the curved image slice 318 is defined by drawing a pair of curved lines 314, 316 on opposite sides of the identified curved structure 312 in the selected plane 310. The distance between the pair of curved lines 314, 316 defines a thickness of the curved image slice 318.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing enhanced visualization of a curved structure by automatically displaying a rendered view of a curved image slice.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method comprising:
identifying, by a processor, a curved structure in three-dimensional medical image data based at least in part on image detection techniques;
selecting, by the processor, a plane in the three-dimensional medical image data based at least in part on the identified curved structure;
automatically defining, by the processor, a curved image slice in the selected plane based at least in part on the identified curved structure and a determined slice thickness;
generating, by the processor, a rendered image of the defined curved image slice having the determined slice thickness; and
presenting, at a display system, the rendered image of the defined curved image slice having the determined slice thickness.

2. The method according to claim 1, comprising acquiring, by an ultrasound device, the three-dimensional medical image data.

3. The method according to claim 1, comprising receiving, by the processor, a selection of a render image display mode to initiate the identification of the curved structure in the three-dimensional medical image data.

4. The method according to claim 1, wherein the curved image slice is defined by drawing a pair of curved lines on opposite sides of the identified curved structure in the selected plane, wherein a distance between the pair of curved lines defines the determined slice thickness of the curved image slice.

5. The method according to claim 1, comprising presenting, at a display system, the selected plane having a pair of curved lines superimposed on opposite sides of the identified curved structure, wherein the pair of curved lines defines the curved image slice having the determined slice thickness.

6. The method according to claim 5, wherein the rendered image and the selected plane are simultaneously presented at the display system, and wherein one or more of the rendered image and the selected plane are dynamically updated by the processor in response to a user input at least one of:
changing a position of the pair of curved lines, and
changing render settings.

7. The method according to claim 1, wherein the curved structure is an endometrium of a uterus.

8. The method according to claim 1, wherein the selected plane is a mid-sagittal plane.

9. The method according to claim 1, wherein the rendered image is generally perpendicular to the selected plane.

10. A system comprising:
a processor configured to:
identify a curved structure in three-dimensional medical image data based at least in part on image detection techniques;
select a plane in the three-dimensional medical image data based at least in part on the identified curved structure;
automatically define a curved image slice in the selected plane based at least in part on the identified curved structure and a determined slice thickness; and
generate a rendered image of the defined curved image slice having the determined slice thickness; and
a display system configured to present the rendered image of the defined curved image slice having the determined slice thickness.

11. The system according to claim 10, wherein the display system is configured to present the selected plane having a pair of curved lines superimposed on opposite sides of the identified curved structure, wherein the pair of curved lines defines the curved image slice having the determined slice thickness.

12. The system according to claim 11, wherein the rendered image and the selected plane are simultaneously presented at the display system, and wherein one or more of the rendered image and the selected plane are dynamically updated by the processor in response to a user input at least one of:
changing a position of the pair of curved lines, and
changing render settings.

13. The system according to claim 10, comprising an ultrasound device configured to acquire the three-dimensional medical image data.

14. The system according to claim 10, wherein the processor is configured to define the curved image slice by drawing a pair of curved lines on opposite sides of the identified curved structure in the selected plane, wherein a distance between the pair of curved lines defines the determined slice thickness of the curved image slice.

15. The system according to claim 10, wherein the curved structure is an endometrium of a uterus.

16. The system according to claim 10, wherein at least one of:
the selected plane is a mid-sagittal plane, and
the rendered image is generally perpendicular to the selected plane.

17. A non-transitory computer readable medium having stored thereon, a computer program having at least one code section, the at least one code section being executable by a machine for causing the machine to perform steps comprising:
identifying a curved structure in three-dimensional medical image data based at least in part on image detection techniques;
selecting a plane in the three-dimensional medical image data based at least in part on the identified curved structure;
automatically defining a curved image slice in the selected plane based at least in part on the identified curved structure and a determined slice thickness;
generating a rendered image of the defined curved image slice having the determined slice thickness; and
displaying the rendered image of the defined curved image slice having the determined slice thickness.

18. The non-transitory computer readable medium according to claim 17, comprising displaying the selected plane having a pair of curved lines superimposed on opposite sides of the identified curved structure, wherein the pair of curved lines defines the curved image slice having the determined slice thickness.

19. The non-transitory computer readable medium according to claim 17, wherein one or more of:
the curved structure is an endometrium of a uterus,
the selected plane is a mid-sagittal plane, and
the rendered image is generally perpendicular to the selected plane.

20. The non-transitory computer readable medium according to claim 17, wherein the curved image slice is defined by drawing a pair of curved lines on opposite sides of the identified curved structure in the selected plane, and wherein a distance between the pair of curved lines defines the determined slice thickness of the curved image slice.

* * * * *